United States Patent
Peschard et al.

(10) Patent No.: US 11,612,556 B2
(45) Date of Patent: Mar. 28, 2023

(54) PEPTIDIC COMPOUNDS, COMPOSITIONS COMPRISING THEM AND USES OF SAID COMPOUNDS, IN PARTICULAR COSMETIC USES

(71) Applicant: SEDERMA, Le Perray en Yvelines (FR)

(72) Inventors: Olivier Peschard, Rambouillet (FR); Anne Doucet, Rambouillet (FR); Richard Leroux, Faverolles (FR); Philippe Mondon, Montrouge (FR)

(73) Assignee: Sederma, Le Perray-en-Yvelines (FR)

( * ) Notice: Subject to any disclaimer, the term of this patent is extended or adjusted under 35 U.S.C. 154(b) by 400 days.

(21) Appl. No.: 15/535,651

(22) PCT Filed: Dec. 14, 2015

(86) PCT No.: PCT/IB2015/059580
§ 371 (c)(1),
(2) Date: Jun. 13, 2017

(87) PCT Pub. No.: WO2016/097965
PCT Pub. Date: Jun. 23, 2016

(65) Prior Publication Data
US 2018/0000717 A1    Jan. 4, 2018

(30) Foreign Application Priority Data
Dec. 16, 2014 (FR) ..................... 1462510

(51) Int. Cl.
| A61K 8/65 | (2006.01) |
| A61Q 19/08 | (2006.01) |
| C07K 14/78 | (2006.01) |

(52) U.S. Cl.
CPC ............... *A61K 8/65* (2013.01); *A61Q 19/08* (2013.01); *C07K 14/78* (2013.01)

(58) Field of Classification Search
None
See application file for complete search history.

(56) References Cited

U.S. PATENT DOCUMENTS

| 3,993,795 A | 11/1976 | Mauron et al. |
| 6,297,354 B1 | 10/2001 | Haviv et al. |
| 7,354,926 B2 | 4/2008 | Lintner |
| 2004/0115766 A1 | 6/2004 | Lintner |
| 2009/0010976 A1 | 1/2009 | Lintner |

FOREIGN PATENT DOCUMENTS

| WO | 9927945 A1 | 6/1999 |
| WO | 02064551 A1 | 8/2002 |
| WO | 02066668 A2 | 8/2002 |
| WO | 2004012650 A2 | 2/2004 |
| WO | 2004024695 A1 | 3/2004 |
| WO | 2010067327 A1 | 6/2010 |
| WO | 2013046137 A2 | 4/2013 |
| WO | 2013105047 A2 | 7/2013 |
| WO | 2013105048 A2 | 7/2013 |

OTHER PUBLICATIONS

Folkers et al. ("Specificity of Design to Achieve Antagonist of LHRH of increasing effectiveness in Therapeutic activity"; Chapter from book, LHRH and its analogs: Contraceptive and Therapeutic Applications, p. 2; pp. 25-36, 1987).*
Pollaro et al. ("Strategies of prolong the plasma residence time of peptide drugs"; MedChem comm Issue 5, 2010).*
JPT Innovative Peptide Solutions (Oct. 29, 2013).*
Plessing et al. ("Enzymatic cleavage of the epsilon-peptide bond in alpha and epsilon substituted glycyl- and phenylalanyl-l-lysine peptides"; Hoppe-Seyler's Zeitschrift Fuer Physiologische Chemie, Walter De Gruyter, Berlin, DE. vol. 363, No. 8 Mar. 1, 1982 p. 279-293).*
Shemyakin ("Primary structure determination of peptides and proteins by Mass spec" 1968).*
Lim et al. ("Site specific fatty acid conjugation to prolong protein half-life in vivo"; J Control Release Sep. 2013. 10: 170(2); 219225).*
Yasutake et al. (Reactivity of human leukocytes elastase and procine pancreatic elastase toward peptide 4-nitroanilides containing model desmosine residues, Evidence that human leukocytes elastase is selective for cros.*
International Search Report and Written Opinion for International Application PCT/IB2015/059580, dated Feb. 24, 2016—11 Pages.
Polycarpo et al., "Pyrrolysine Analogues as Substrates for Pyrrolysyl-tRNA Synthetase", FEBS Letters, vol. 580, No. 28-29, Dec. 11, 2006, pp. 6695-6700.

* cited by examiner

*Primary Examiner* — Julie Ha
*Assistant Examiner* — Tara L Martinez
(74) *Attorney, Agent, or Firm* — RatnerPrestia

(57) ABSTRACT

The peptidic compound comprises at least an aminoacid which is lysine, ornithine, diaminopropionic acid or diaminobutyric acid or a derivative of these aminoacids, on which a carboxylic acid is grafted via a peptidic bound on the nitrogen of the lateral chain, said carboxylic acid comprising a (poly)cycle or (poly)heterocycle. Preferably, the grafted carboxylic acid is an aminoacid or a derivative, in particular selected from, a proline, a hydroxyproline or pyroglutamic acid.

The peptidic compound can stimulate the synthesis of the main molecules constituting the extracellular matrix of the skin, especially collagen 1 and 4 and elastin. It can be used for topical cosmetic treatment such as a global anti-aging treatment, or for specific activities, including anti-wrinkles, moisturizing, to improve the mechanical properties of the skin, firmness/tone/elasticity/flexibility, to increase density and volume of the skin, improve skin radiance, for a restructuring effect and/or to fight stretch marks.

14 Claims, 1 Drawing Sheet
Specification includes a Sequence Listing.

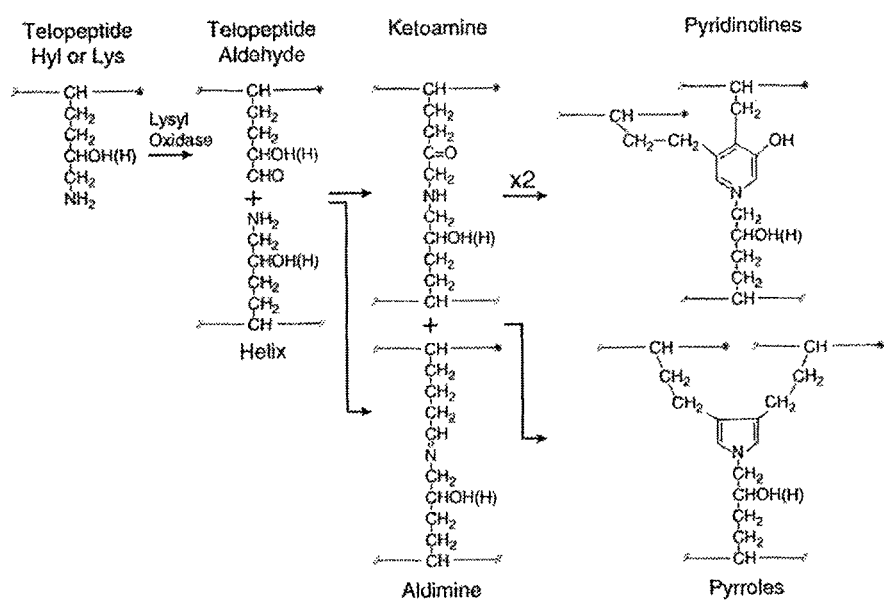

SEQUENCE LISTING

<160> NUMBER OF SEQ ID NOS: 20

<210> SEQ ID NO 1
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 1

Lys Thr Thr Lys Ser
1               5

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain

<400> SEQUENCE: 2

Gly Gln Pro Arg
1

<210> SEQ ID NO 3
<211> LENGTH: 4
<212> TYPE: PRT
<213> ORGANISM: artificial sequence
<220> FEATURE:
<223> OTHER INFORMATION: synthetic peptide

<400> SEQUENCE: 3

Lys Thr Phe Lys
1

<210> SEQ ID NO 4
<211> LENGTH: 4
<212> TYPE: PRT
<213> ORGANISM: artificial sequence
<220> FEATURE:
<223> OTHER INFORMATION: synthetic peptide

<400> SEQUENCE: 4

Lys Gly His Lys
1

<210> SEQ ID NO 5
<211> LENGTH: 6
<212> TYPE: PRT
<213> ORGANISM: artificial sequence
<220> FEATURE:
<223> OTHER INFORMATION: synthetic peptide

<400> SEQUENCE: 5

Gly Lys Thr Thr Lys Ser
1               5

<210> SEQ ID NO 6
<211> LENGTH: 4
<212> TYPE: PRT

```
<213> ORGANISM: artificial sequence
<220> FEATURE:
<223> OTHER INFORMATION: synthetic peptide

<400> SEQUENCE: 6

Arg Ser Arg Lys
1

<210> SEQ ID NO 7
<211> LENGTH: 4
<212> TYPE: PRT
<213> ORGANISM: artificial sequence
<220> FEATURE:
<223> OTHER INFORMATION: synthetic peptide

<400> SEQUENCE: 7

Gly Gln Pro Arg
1

<210> SEQ ID NO 8
<211> LENGTH: 5
<212> TYPE: PRT
<213> ORGANISM: artificial sequence
<220> FEATURE:
<223> OTHER INFORMATION: synthetic peptide

<400> SEQUENCE: 8

Lys Thr Thr Lys Ser
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Val Gly Val Ala Pro Gly
1               5

<210> SEQ ID NO 10
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by an elaidoyl chain on the N
      terminal end

<400> SEQUENCE: 10

Lys Thr Phe Lys
1

<210> SEQ ID NO 11
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Amidation by a Palmitoyl chain

<400> SEQUENCE: 11
```

Tyr Gly Gly Phe Leu
1               5

<210> SEQ ID NO 12
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Amidation by a palmitoyl chain

<400> SEQUENCE: 12

Tyr Gly Gly Phe Pro
1               5

<210> SEQ ID NO 13
<211> LENGTH: 6
<212> TYPE: PRT
<213> ORGANISM: artificial sequence
<220> FEATURE:
<223> OTHER INFORMATION: synthetic peptide

<400> SEQUENCE: 13

His Leu Asp Ile Ile Trp
1               5

<210> SEQ ID NO 14
<211> LENGTH: 6
<212> TYPE: PRT
<213> ORGANISM: artificial sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is aTryptoline-3-carboxylic acid residu
      (Tpi)

<400> SEQUENCE: 14

His Leu Asp Ile Ile Xaa
1               5

<210> SEQ ID NO 15
<211> LENGTH: 6
<212> TYPE: PRT
<213> ORGANISM: artificial sequence
<220> FEATURE:
<223> OTHER INFORMATION: Synthetic peptide

<400> SEQUENCE: 15

His Leu Asp Ile Ile Phe
1               5

<210> SEQ ID NO 16
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (6)..(6)

```
<223> OTHER INFORMATION: NH2

<400> SEQUENCE: 16

Glu Glu Met Gln Arg Arg
1               5

<210> SEQ ID NO 17
<211> LENGTH: 5
<212> TYPE: PRT
<213> ORGANISM: artificial sequence
<220> FEATURE:
<223> OTHER INFORMATION: synthetic peptide

<400> SEQUENCE: 17

Tyr Ala Gly Phe Leu
1               5

<210> SEQ ID NO 18
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation

<400> SEQUENCE: 18

Ala His Ser His
1

<210> SEQ ID NO 19
<211> LENGTH: 6
<212> TYPE: PRT
<213> ORGANISM: artificial sequence
<220> FEATURE:
<223> OTHER INFORMATION: synthetic peptide

<400> SEQUENCE: 19

Ser Ile Lys Val Ala Val
1               5

<210> SEQ ID NO 20
<211> LENGTH: 6
<212> TYPE: PRT
<213> ORGANISM: artificial sequence
<220> FEATURE:
<223> OTHER INFORMATION: synthetic peptide

<400> SEQUENCE: 20

Gly Pro Gln Gly Pro Gln
1               5
```

PEPTIDIC COMPOUNDS, COMPOSITIONS COMPRISING THEM AND USES OF SAID COMPOUNDS, IN PARTICULAR COSMETIC USES

CROSS-REFERENCE TO RELATED APPLICATIONS

This application is the U.S. national phase under 35 U.S.C. § 371 of International Application No. PCT/IB2015/059580, filed Dec. 14, 2015, and claims priority to FR Patent Application No. 1462510, filed Dec. 16, 2014, the contents of each of which are incorporated by reference in their entireties.

TECHNICAL FIELD

The present invention relates to peptidic compounds, compositions comprising them, and cosmetic or dermopharmaceutical uses of said peptides. It relates more particularly to compounds and compositions for treating the skin and appendages of mammals, humans or animals.

A peptidic compound according to the invention is defined as comprising at least one amino acid and more usually from 2 to 10 amino acids, derivatives and analogs linked by peptidic bonds.

The invention concerns cosmetics (topical or oral), hygiene and personal care and dermo-pharmacy industries.

BACKGROUND ART

Small peptides or peptidic compounds are formed by enzymatic degradation in the extracellular matrix of the skin and it has been shown that these peptides or compounds, which were called "matrikines", were able to regulate the cellular activity because they had an important signal function. Many peptides or peptide mixtures obtained by extraction or synthesis have been thus proposed as active ingredients in cosmetics to mimic these processes. Examples include the well-known lipopeptide Pal-KTTKS (SEQ ID NO: 1) marketed under the MATRIXYL™ trademark and the Pal-GHK/Pal-GQPR (SEQ ID NO: 2) mixture marketed under the trademark MATRIXYL3000™, corresponding to fragments of collagen, for which thanks to in vitro tests a stimulation of collagen synthesis could be actually measured and through in vivo tests a significant improvement on various factors like the firmness, elasticity, density, thickness, microrelief of the skin (wrinkles and fine lines), etc. could be measured.

Thus peptide became essential and promising active ingredients especially in the cosmetics industry where new compounds are always sought, capable of beautifying skin and its appendages, that is to say improving their general condition by correcting imperfections.

The present inventors are more particularly interested in the research of novel peptidic compounds having an activity on the main molecules constituents of the skin extracellular matrix (ECM) which quantity and quality decrease with aging (chronological or premature), and more particularly novel peptidic compounds mainly active on the synthesis of collagen which is the major protein of skin. Loss of density and thickness of dermis are closely related to a reduced synthesis of the macromolecules with aging by fibroblasts, the cells responsible for their production. Collagen I is the most abundant protein in the dermis. It is essential in obtaining a firm skin. Elastin is synthesized and secreted in the dermal extracellular space. It is the major component up to 90% of elastic fibers.

Fibronectin is a glycoprotein also present in the extracellular matrix and which plays a key role in cell adhesion to the extracellular matrix. It can simultaneously bind to the cell and to other molecules of the extracellular matrix, such as collagen or another fibronectin molecule. To this aim, the fibronectin molecules assemble together to form adhesive elastic fibers on the surface of many cells. This determines the mechanical properties (elasticity, flexibility and firmness) of the skin.

The increase in collagen IV and laminins is also sought. It helps to restore/enhance the dermal/epidermal junction (DEJ). Collagen IV forms a two-dimensional network and constitutes a major component of the dermal/epidermal junction. Laminins are also contained in the basal layer and are involved in anchoring cell surfaces to basal lamina.

These two essential components ensure together that keratinocytes of the basal lamina have a better anchoring and contribute to maintaining the flexibility of the skin.

The reduction in protein synthesis with aging is felt at the DEJ level: collagen of type IV is more fragmented and at the same time less produced, as well as laminins, resulting in some areas in an impaired DEJ and poorer communication between melanocytes, keratinocytes and DEJ, and less flexibility of the system. The interest to stimulate the synthesis of these two proteins thus appears clearly.

The stimulated synthesis of these molecules by the peptidic compound will generate results on the beautifying and general condition of the skin, at the level of its mechanical properties: a skin that will be denser, thicker, replumped, firmer, more toned, more supple and elastic, the peptidic compound having a volumizing, plumping effect and thus anti-wrinkles, and also regarding the perception of skin complexion, its homogeneity and brightness.

Many peptides, peptidic compounds or mixtures thereof having properties on the ECM and anti-aging applications have already been proposed, including by the Applicant, as Pal-KTTKS (SEQ ID NO: 1) sold under the MATRIXYL™ trademark, the Pal-GHK and Pal-GQPR (SEQ ID NO: 2) mixture sold under the MATRIXYL 3000™ trademark or more recently the Pal-KMO2K sold under the trademark MATRIXYL Synthé'6™ (MO2 corresponding to a dioxygenated methionine). Other known peptides having a cosmetic action, in particular on the synthesis of the compounds of the ECM are mentioned below in the specification.

The present invention aims to propose other peptidic compounds capable of improving the general condition of the skin and its appendages, and particularly peptidic compounds active on the synthesis of the dermal ECM proteins. It also aims to provide sufficiently effective peptidic compounds to be used alone or in combination, in proportions of a few ppm, and that can be used as a topical composition, in particular cosmetic composition. Preferably, the present invention also aims to provide peptidic compounds active on the most possible targets (in particular different types of collagen, elastin, fibronectin, laminin and hyaluronic acid) to provide the best and complete possible cosmetic benefit.

BRIEF DESCRIPTION OF THE DRAWING

The FIGURE shows how the lysine of a collagen peptidic chain, under the action of the lysyl hydroxylase, is transformed into hydroxylysine (Hyl).

DETAILED DESCRIPTION OF EMBODIMENT

The present invention provides a peptidic compound that may be used in cosmetics and dermatology comprising at least one amino acid selected from lysine, a lysine analog and a hydroxylated derivative of these amino acids, onto which a carboxylic acid comprising at least one cycle or a heterocycle is grafted by peptidic bond on the nitrogen of side chain.

As shown in Table 1 below, ornithine, diaminobutyric acid and diaminopropionic acid are lysine analogs according to the present invention, comprising respectively a side chain of 3, 2 and 1 carbon atom(s) instead of 4 in the lysine and terminating by an amine group NH₂, the number of atoms acting as a longer or shorter spacer. According to the invention, it is on this lateral amine function that a carboxylic acid comprising at least one cycle or heterocycle is grafted.

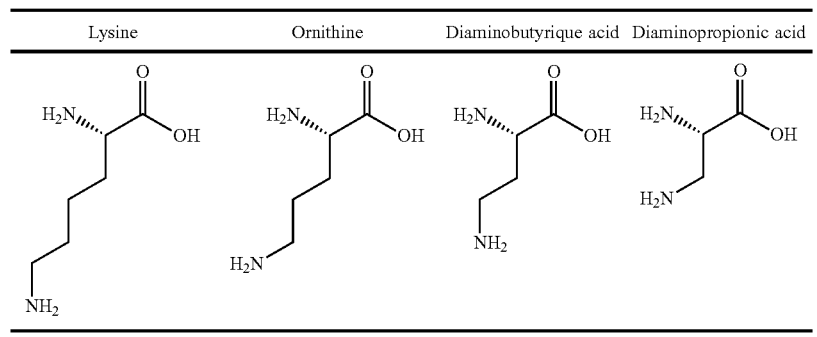

The hydroxylated derivatives comprise for example hydroxylysine:

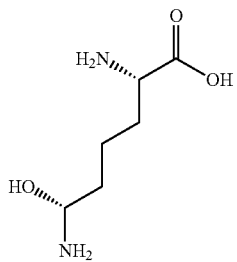

According to the invention, "at least one ring or heterocycle" means a monocycle or polycycle having 2 or 3 joined cycles, each cycle being a carbon cycle of 5, 6 or 7 atoms, aromatic or not, which may contain a N, O or S hetero atom, said cycle or heterocycle which may contain an —OH, —O—, —CO—, —S—, —N═, —NH— or —N═C—NH— function, as well as a charged nitrogen function.

According to the invention, the charged nitrogen function corresponds to —N⁺(r₁)═ or —N⁺(r₁, r₂)-; r₁ and r₂, independently from each other, being alkyl radicals, preferably Me, Et, Pr and Bu.

Preferably according to the invention, the cycle or heterocycle contains 5 or 6 atoms.

The present invention is based on the fact that the lysine is involved very predominantly in the cross-linking of the fibrils of collagen, and that this cross-linking is essential for a good cohesion of the various constituents of the skin.

With reference to the FIGURE, the lysine of a collagen peptidic chain, under the action of the lysyl hydroxylase, is transformed into hydroxylysine (Hyl). The lysyl oxidase (LOX) then converts the amine function (—NH₂) of the lysine (or the hydroxylysine) into an aldehyde (—CHO) that reacts spontaneously with another lysine (or hydroxylysine) to give an immature cross-link between the two peptidic chains (Hyl+Hyl→ketoamine; Lys+Hyl→aldimine). It is called an immature crosslink of two chains because the aldimine functions (—N═CH—) or ketoamine (—C═O—CH₂—NH—) can further react with a third lysine (or Hyl) to form a trivalent mature crosslink having a nitrogen ring containing 5 or 6 links which will no more react and will maintain between them 3 collagen chains. There is also another possibility of reaction of the aldehyde form of the lysine (═Allysine) (and/or hydroxylysine═hydroxyallysine) on itself (aldolisation reaction) which also produces a divalent cross-link.

During degradation of the collagen of the extracellular matrix by metalloproteinases (MMPs), small peptides or peptidic compounds are thus formed among other things in the matrix, that have one or more lysines, bearing a ring on the side chain of the lysine.

The present inventors have discovered that such peptides having a lysine to which is grafted a (poly) (hetero)cycle could also serve as a signal, such as the matrikines, for the renewal of collagen and/or the extracellular matrix.

The detailed description of in vitro tests given below shows that such peptidic compounds actually exhibit activity on the synthesis of molecule markers of the ECM. The compounds are active from a few ppm, and may be used individually or in combination to improve the appearance and the general state of the skin and its appendages, and in particular for the treatment and/or prevention of signs of aging and/or imperfections of skin and its appendages. The inventors have shown that the peptidic compounds according to the invention exhibited in particular a stimulatory activity on synthesis of collagen I and IV, elastin, fibronectin, laminin and hyaluronic acid.

Comparative tests also show the superiority of the peptidic compounds of the invention on these syntheses compared to ungrafted peptides.

It was also demonstrated that these peptidic compounds showed an improvement of their physicochemical properties, in particular their stability.

More particularly, the peptidic compound of the invention responds to the following general formula I:

$$X\text{-}(AA)_n\text{-}(AA)^*\text{-}(AA)_m\text{-}Z \qquad (I)$$

Wherein:
(AA)* is lysine (K*), ornithine (Orn*), diaminopropionic acid (Dap*) or diaminobutyric acid (Dab*) or a hydroxylated derivative of these aminoacids on which a carboxylic acid is grafted by peptidic bound on the nitrogen of the lateral chain, said carboxylic acid comprising at least a carbon cycle or heterocycle with 5, 6 or 7 atoms, aromatic or not, which said cycle or heterocycle can contain an —OH, —O—, —CO—, —S—, —N=, —NH— or —N=C—NH— function, as well as a charged nitrogen function;

n=0, 1, 2, 3 or 4;

m=0, 1, 2, 3 or 4;

AA=(AA)* or an aminoacid selected from alanine (A, Ala), cysteine (C, Cys), aspartic acid (D, Asp), glutamic acid (E, Glu), phenylalanine (F, Phe), glycine (G, Gly), histidine (H, His), isoleucine (I, Ile), lysine (K, Lys), leucine (L, Leu), methionine (M, Met), asparagine (N, Asn), proline (P, Pro), glutamine (Q, Gln), arginine (R, Arg), serine (S, Ser), threonine (T, Thr), valine (V, Val), tryptophan (W, Trp) and tyrosine (Y, Tyr), their derivatives or analogs; the AA being selected independently from each other when n+m>1;

At the N terminal end, X is selected from H, —CO—R, and —SO$_2$—R$_1$;

At the C terminal end, Z is selected from OH, OR$_1$, NH$_2$, NHR$_1$ ou NR$_1$R$_2$; and R$_1$ and R$_2$ being, independently from each other, selected from an alkyle, aryle, aralkyle, alkylaryl, alkoxy and aryloxy radical, that can be linear, branched, cyclic, polycyclic, unsaturated, hydroxylated, carbonylated, phosphorylated and/or sulphated, which said radical can comprise in its skeleton a heteroatom, in particular O, S and/or N.

In formula (I), the aminoacid AA is preferably (AA)* or an aminoacid selected from:

Glycine (G, Gly), Proline (P, Pro) or Lysine (K, Lys), which are the most common amino acids in collagens;

their hydroxylated derivatives, like hydroxyproline (Hyp) and hydroxylysine (Hyl);

the aminoacids having an alcohol function such as serine (S, Scr), threonine (T, Thr) and tyrosine (Y, Tyr); and the other natural aminoacids comprising a cycle, namely histidine (H, His) and phenylalanine (F, Phe).

More preferably, in formula (I), the aminoacid AA is (AA)* or glycine (G, Gly), histidine (H, His) or lysine (K, Lys), or their hydroxylated derivatives; more preferably the aminoacid AA is selected from glycine (G, Gly), histidine (H, His) and lysine (K, Lys).

According to the invention, the grafted carboxylic acid of (AA)* may be a coded aminoacid comprising a (poly)cycle or (poly)heterocycle responding to the definition of the invention given above, namely selected from:

| Grafted carboxylic acid of (AA)* | Peptidic compound: p = 1, 2, 3 ou 4 |
|---|---|
| Proline (P, Pro) | 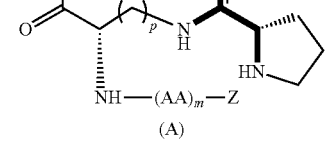 (A) |
| Hydroxyproline (Hyp) | 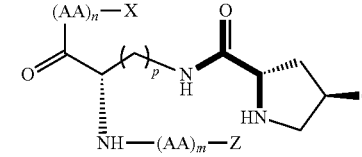 (B) |
| Pyroglutamic acid (Pyr), | 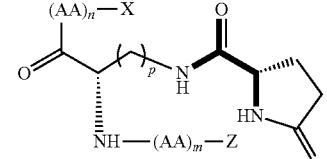 (C) |
| Histidine (H, His), | 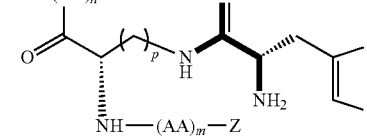 (D) |
| Phenylalanine (F, Phe), | 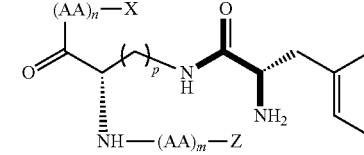 (E) |

| Grafted carboxylic acid of (AA)* | Peptidic compound: p = 1, 2, 3 ou 4 |
|---|---|
| Tyrosine (Y, Tyr), and | 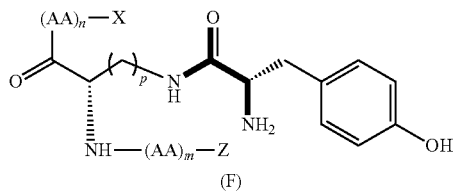 (F) |
| Tryptophan (W, Trp) | 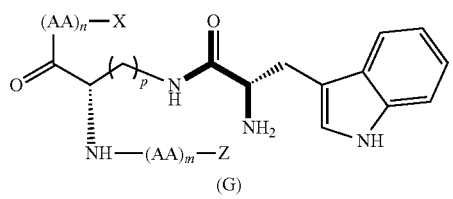 (G) |

According to the invention, the grafted carboxylic acid of (AA)* can also be a derivative or analog of these aminoacids, such as:

| Grafted carboxylic acid of (AA)* | Peptidic compound p = 1, 2, 3 or 4 |
|---|---|
| Tetrahydroisoquinoline-3 carboxylic acid (Tic), which is a derivative of phenylalanine. | 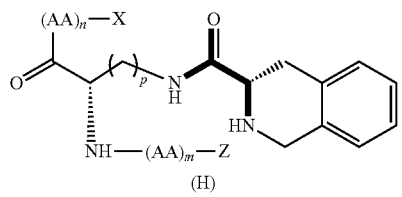 (H) |
| Tetrahydronorharman-3 carboxylic acid (Tpi), which is a derivative of tryptophane. | 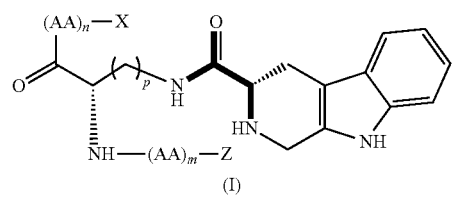 (I) |

As preferred examples of carboxylic acid according to the invention which are not aminoacids or derivatives thereof, the following acids may also be mentioned:

| Grafted carboxylic acid of (AA)* | Peptidic compound p = 1, 2, 3 or 4 |
|---|---|
| Pipecolic acid (Hpr) (Proline analog) | 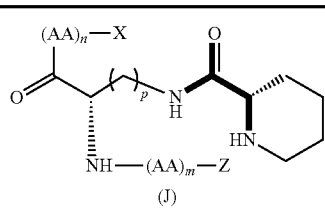<br>(J) |
| Nipecotic acid (Nip) (Proline analog) | 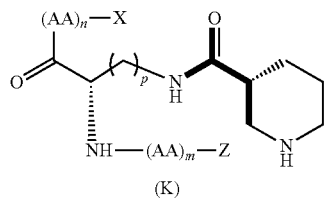<br>(K) |
| Nicotinic acid (Nic) | 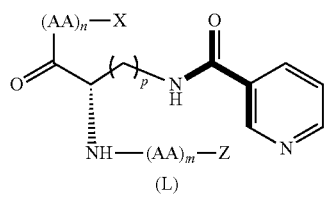<br>(L) |
| Picolinic acid (Pic) | 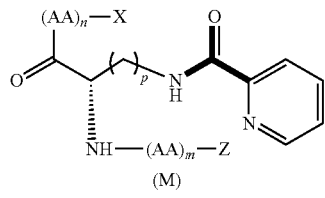<br>(M) |
| 4-imidazole carboxylic acid (Im4COOH) | 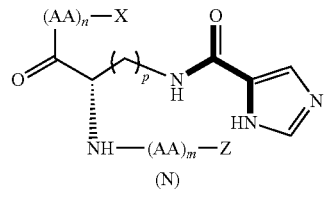<br>(N) |
| Stachydrine (Sta) | 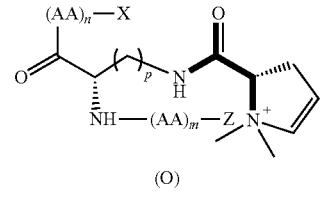<br>(O) |
| Betonicine (Btn) | 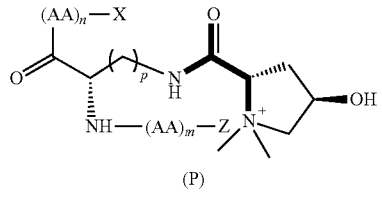<br>(P) |
| Homarine (Hom) | 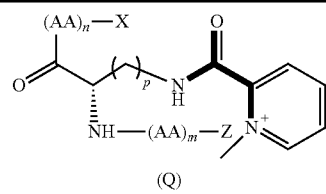<br>(Q) |

The invention thus encompasses preferably the compounds having the following formula (II):

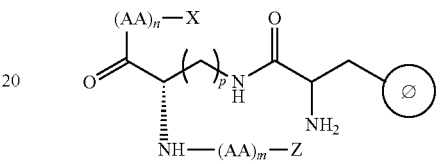

Wherein:
(AA); X; Z; n, m and p, are as recited above; and
Ø=a cycle or polycycle, each cycle having 5 or 6 carbon atoms, aromatic or not, and which can comprise one or more N heteroatom charged or not;
Or the following formula (III):

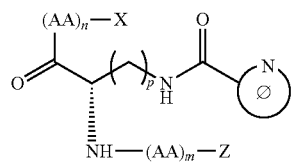

Wherein:
(AA); X; Z; n, m and p, are such as recited above; and
Ø=a cycle or polycycle, each cycle having 5 or 6 carbon atoms, aromatic or not, and which can comprise one or more N heteroatom charged or not;
As previously, the charged nitrogen form correspond to —$N^+(r1)$= or —$N^+(r1,r2)$-; r1 and r2, independently from each other, being alkyl radicals, preferably Me, Et, Pr and Bu.

Preferably in formula III, the nitrogen of the Ø cycle is in β or γ with regard to the carbonyl function on which is bound said Ø cycle.

Preferably according to the invention, (AA)* is a grafted lysine (K*), the compound having thus the general formula IV: X-$(AA)_n$-K*-$(AA)_m$-Z (IV)

More preferably the peptidic compound K* is selected from:
K*=K(P): a proline (P, Pro) grafted on a lysine (K, Lys);
K*=K(Hyp): an hydroxyproline (Hyp) grafted on a lysine (K, Lys); and
K*=K(Pyr): a pyroglutamic acid (Pyr) grafted on a lysine (K, Lys).

According to the invention «small» peptidic peptides are preferred corresponding to n+m comprised between 1 and 5 (dipeptides to hexapeptides), and more preferably n+m=1 or 2 (dipeptides or tripeptides).

Preferably n=0.

According to other preferred features of the invention, in above formula (I):

R$_1$ and/or R$_2$ is an alkyle chain comprising 1 to 24 carbon atoms, preferably a lipophilic alkyl chain comprising 3 to 24 carbon atoms; and/or X is an CO—R$_1$ acyl group and Z is selected from OH, OMe, OEt and NH$_2$, preferably Z is OH; X is preferably selected from an octanoyl (C8), decanoyl (C10), lauroyl (C12), myristoyl (C14), palmitoyl (C16), stearoyl (C18), biotinoyl, claidoyl, olcoyl and lipoyl; more preferably selected from a lauroyl (C12), myristoyl (C14) and palmitoyl (C16); and/or Z is OH and X is selected from a myristoyl (C14) or a palmitoyl (C16).

The preferred compounds according to the invention are the following tripeptidic compounds:

X—K(P)-HG-Z, X—K(Pyr)-HG-Z, X—K(Hyp)-HG-Z, X—K(P)-GH—Z, X—K(Pyr)-GH—Z and X—K(Hyp)-GH—Z And more particularly the following peptidic compounds:

Pal-K(P)-HG-OH, Pal-K(Pyr)-HG-OH, Pal-K(Hyp)-HG-OH,

Pal-K(P)-GH-OH, Pal-K(Pyr)-GH-OH, Pal-K(Hyp)-GH-OH.

The present invention also provides a method for increasing the activity on the synthesis of the ECM macromolecules of the skin of a peptidic compound comprising at least one lysine (K, Lys), ornithine (Orn), diaminopropionic acid (Dap) or diaminobutyric acid (Dab) or a derivative of these amino acids, wherein a carboxylic acid comprising at least one carbon cycle or heterocycle comprising 5, 6 or 7 atoms, aromatic or not, is grafted by peptidic bond on the nitrogen of the side chain of the at least one lysine (K, Lys), ornithine (Orn), diaminopropionic acid (Dap) or diaminobutyric acid (Dab) or derivative of these amino acids, said cycle or heterocycle which may comprise a —OH, —O—, —CO—, —S—, —N=, —NH—, —N=C—NH— function as well as a charged nitrogen function.

This method is preferably applied to peptidic compounds having 1 to 9 aminoacids.

This method can be applied to known peptides in cosmetics comprising for example a lysine as in the following peptidic sequences (X and Z being as recited above):

X-KT-Z,
X-GHK—Z,
X—KPK—Z,
X—KFK—Z,
X-KAvaK—Z (Ava=5-aminovaleric acid),
X-KM02K—Z (Matrixyl Synthe'6™) (M0$_2$=dioxygenated methionine),
X-KTFK—Z (SEQ ID NO: 3)
X-KGHK—Z, (Kollaren 6™ or Folixyl™ or Chronoline™)(SEQ ID NO: 4)
X-KTTKS—Z (Matrixyl™) (SEQ ID NO: 1), or
X-GKTTKS—Z (SEQ ID NO: 5)

In these peptides, one, several or each lysine (K, Lys), ornithine (Om), diaminopropionic acid (Dap) or diaminobutyric acid (Dab) can be grafted, and preferably all.

More preferably according to the invention, the carboxylic acids that will be chosen to be grafted will be the proline (P, Pro) or pyroglutamic acid (Pyr).

The peptides of the invention may be optically pure, or be composed of L or D isomers or a mixture thereof. L isomers, which are those found in nature, may be preferred.

The peptides may be in the form of salts, especially salts of hydrochloric acid or acetic acid, or any salts commonly used in cosmetics.

The present invention also encompasses derivatives (with modification and/or addition of a chemical function but without change in the carbon skeleton) and analogs (with modification and/or addition of a chemical functional group but with an additional change in the carbon skeleton), complexes with other species such as metal ion (eg copper, zinc, manganese, magnesium, and others).

The present invention also provides a cosmetic or dermatological composition (topical or oral) comprising as active ingredient at least one peptidic compound according to the invention and as recited above in a physiologically acceptable medium.

The invention also provides the use of at least one peptidic compound according to the invention for the preparation of a composition for a dermatological treatment, as well as the use of at least one peptidic compound according to the invention or of a composition according the invention comprising said compound for a cosmetic treatment, in particular topical, to improve the general state of the skin and/or its appendages, said treatment being intended to stimulate the synthesis of at least one of the molecules of the extracellular dermal matrix.

According to the invention the proposed cosmetic treatment helps to fight against aging and/or imperfections of skin and/or its appendages, such as a:

Global anti-aging treatment; and/or

Anti-wrinkles and fine lines treatment (smoothed skin relief, filled wrinkles), and/or A treatment improving the mechanical properties of skin: firmness/tone/elasticity/flexibility, and/or A treatment increasing skin density (restructuring effect); and/or A treatment increasing the volume of skin (plumping effect); and/or A treatment to fight against the appearance of stretch marks, and/or A moisturizing treatment, and/or An anti-spot treatment, and/or A treatment to improve the homogeneity and/or radiance of skin, and/or A treatment acting on the pigmentation of the skin.

According to the dosage of the excipient and the peptidic compound(s), the composition of the invention will constitute for example a concentrated active ingredient or a final composition less concentrated directly for the client or patient.

"Physiologically acceptable medium" means according to the present invention, without limitation, an aqueous or hydro-alcoholic solution, a water-in-oil emulsion, an oil-in-water emulsion, a micro-emulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hairs), scalp and skin of mammals, particularly human, compositions which may be ingested, or injected into the skin, without risk of toxicity, incompatibility, instability, allergic response, and others. This "physiologically acceptable medium" forms what is commonly called the excipient of the composition.

The peptidic compounds of the invention can be solubilized in a lipophilic or hydrophilic matrix with optionally a solubilizer, according to the envisaged use.

The peptidic compound(s) may be combined with other active ingredients at effective concentrations that can act synergistically or additionally for reinforcing and achieving the desired effects described for the invention, such as the following agents: anti-aging, anti-fine lines and wrinkles, lightening, pro-pigmenting, hydrating, moisturizing, humectant, slimming, exfoliating, anti-acne, anti-redness, anti-inflammatories, anti-oxidant/radical scavengers, acting on brightness of complexion, anti-glycation, volumizing, restructuring, anti-carbonylation, dermo-relaxing, anti-hair regrowth, action on stratum corneum, dermal-epidermal junction, HSP protein production, firmness, elasticity and tone of skin, hair growth (eyelashes and eyebrows), eye contours (dark circles and under eye bags), promoting blood circulation, other peptides, vitamins etc. These active ingredients may be obtained from plant materials, such as classical plant extracts or products of plant cell culture or fermentation.

The composition according to the invention may be applied to the face, body, neckline, scalp, hair, eyelashes, body hair, in whatever form or carriers known to those skilled in the art, in particular in the form of solution, dispersion, emulsion, paste, or powder, individually or as a premix or in vehicles individually or as a premix in vectors such as macro-, micro-, or nano-capsules, macro-, micro- or nano-spheres, liposomes, oleosomes or chylomicrons, macro-, micro-, or nanoparticles or macro-, micro- or nano-sponges, micro- or nano-emulsions or adsorbed on organic polymer powders, tales, bentonites, spores or exines, and other inorganic or organic supports.

In cosmetics, applications can be offered particularly in skincare ranges for the face, body, hair and body hairs, and in make-up ranges, including for eyebrows and eyelashes.

In general, the peptidic compounds according to the present invention may be used in any form, in a form bound to or incorporated in or absorbed in or adsorbed on macro-, micro-, and nanoparticles, or macro-, micro-, and nano-capsules, for the treatment of textiles, natural or synthetic fibers, wools, and any materials that may be used for clothing or underwear for day or night intended to come into contact with the skin, handkerchiefs or cloths, to exert their cosmetic effect via this skin/textile contact and to permit continuous topical delivery.

The CTFA («International Cosmetic Ingredient Dictionary & Handbook» (15th Ed. 2014) published by «the Personal Care Products council», ex- «the Cosmetic, Toiletry, and Fragrance Association, Inc.», Washington, D.C.), describes a non-limited wide variety of cosmetic and pharmaceutical ingredients commonly used in the skin care industry, which are suitable for use as additional ingredients in the compositions according to the present invention.

Further additional skin care actives that are particularly useful can be found in the commercial literature of Sederma and on the website www.sederma.com.

The following commercial actives can also be mentioned, as examples: betaine, glycerol, Actimoist Bio 2™ (Active organics), AquaCactcen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of *Boswellia serrata* known under the commercial name Boswellin™, Deepaline PVB™ (Seppic), Syn-AKE™ (Pentapharm), Ameliox™, Bioxilift™ (Silab), PhytoCellTec™ Argan (Mibelle), Papilactyl D™ (Silab), Preventhelia™ (Lipotec), Subliskin™ (Sederma), Venuceane™ (Sederma), Moist 24™ (Sederma), Vegesome Moist 24™ (Sederma), Essenskin™ (Sederma), Juvinity™ (Sederma), Revidrat™ (Sederma), Resistem™ (Sederma), Chronodyn™ (Sederma), Kombuchka™ (Sederma), Chromocare™ (Sederma), Calmosensine™ (Sederma), Glycokin factor S™ (Sederma), Biobustyl™ (Sederma), Idealift™ (Sederma), Ceramide 2™, Ceramide A2™ et Ceramide HO3™ (Sederma), Legance™ (Sederma), Intenslim™ (Sederma), Prodizia™ (Sederma), Beautifeye™ (Sederma), NG-shea butter unsaponifiables (natural grade)(Sederma), Zingerslim™ (Sederma), Meiritage™ (Sederma), Senestem™ (Sederma), Sebuless™ (Sederma), Majestern™ (Sederma), Apiscalp™ (Sederma), Rubistem™ (Sederma) or mixture thereof.

Among other plant extracts which can be combined with the peptide of the invention, there may more particularly be mentioned extracts of Ivy, in particular English Ivy (*Hedera Helix*), of *Bupleurum chinensis*, of *Bupleurum falcatum*, of arnica (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum perforatum*), of butcher's-broom (*Ruscus aculeatus* L), of European meadowsweet (*Filipendula ulmaria* L), of big-flowered Jarva tea (*Orthosiphon Staminicus Benth*), of algae (*Fucus vesiculosus*), of birch (*Betula alba*), of green tea, of cola nuts (*Cola nipida*), of horse-chestnut, of bamboo, of *Centella asiatica*, of heather, of fucus, of willow, of mouse-ear, of escine, of cangzhu, of chrysanthellum indicum, of the plants of the *Armeniacea* genus, *Atractylodis platicodon, Sinnomenum, Pharbitidis, Flemingia*, of *Coleus* such as *C. forskohlii, C. blumei, C. esquirolii, C. scutellaroides, C. xanthantus* and *C. barbatus*, such as the extract of root of *Coleus barbatus*, extracts of *Ballote*, of *Guioa*, of *Davallia*, of *Terminalia*, of *Barringtonia*, of *Trema*, of antirobia, cecropia, argania, dioscoreae such as *Dioscorea opposita* or Mexican, extracts of *Ammi visnaga*, of *Siegesbeckia*, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia Cordifolia*), and Guggal (extracted from plants of the genus *Commiphora*, particularly *Commiphora Mukul*), kola extract, chamomile, red clover extract, *Piper methysticum* extract (Kava Kava™ from SEDERMA), *Bacopa monieri* extract (Bacocalmine™ from SEDERMA) and sea whip extract, extracts of *Glycyrrhiza glabra*, of mulberry, of melaleuca (tea tree), of *Larrea divaricata*, of *Rabdosia rubescens*, of *Euglena gracilis*, of *Fibraurea recisa hirudinea*, of *Chaparral sorghum*, of sun flower extract, of *Enantia chlorantha*, of Mitracarpe of *Spermacocea* genus, of *Buchu barosma*, of *Lawsonia inermis* L., of Adiantium *Capillus-Veneris* L., of *Chelidonium majus*, of *Luffa cylindrica*, of Japanese Mandarin (*Citrus reticulata Blanco* var. *unshiu*), of *Camelia sinensis*, of *Imperata cylindrica*, of *Glaucium flavum*, of *Cupressus Sempervirens*, of *Polygonatum multiflorum*, of loveyly hemsleya, of *Sambucus nigra*, of *Phaseolus lunatus*, of *Centaurium*, of *Macrocystis pyrifera*, of *Turnera diffusa*, of *Anemarrhena asphodeloides*, of *Portulaca pilosa*, of *Humulus lupulus*, of *Coffea Arabica*, of flex *Paraguariensis*, or of *Globularia cordifolia*, of *Albizzia julibrissin*, of *Oxydendron arboretum*, of *Zingimber zerumbet* Smith, of *Astragalus membranaceus*, of *Atractylodes macrocephalae*, of *Plantago lanceolata*, of *Leontopodium alpinum*, of *Mirabilis jalapa* or of *Apium graveolens*.

The compositions of the present invention may include other peptides or peptidic compounds, including, without limitation, di-, tri-, tetra-, penta- and hexapeptides and their derivatives. According to a particular embodiment, the concentration of the additional peptide, in the composition, ranges from $1 \times 10^{-7}$% and 20%, preferably from $1 \times 10^{-6}$% and 10%, preferably between $1 \times 10^{-5}$% and 5% by weight. According to the present invention, the term "peptide" refers to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (beta-AH), YR, VW, NF, DF, KT, RT, KC, CK, KP, KK or TT. Suitable tripeptides for use herein include, but are not limited to RKR, HGG, GHK, GKH, GGH, GHG, KFK, KPK, KMOK, KMO2K or KAvaK. Suitable tetrapeptides for use herein include but are not limited to RSRK (SEQ ID NO: 6), GQPR (SEQ ID NO: 7) or KTFK (SEQ ID NO: 3). Suitable pentapeptides include, but are not limited to KTTKS (SEQ ID NO: 8). Suitable hexapeptides include but are not limited to GKTTKS (SEQ ID NO: 5) and VGVAPG (SEQ ID NO: 9).

Other suitable peptides for use herein include, but are not limited to: lipophilic derivatives of peptides, preferably palmitoyl derivatives, and metal complexes as aforementioned (e.g. copper complex of the tripeptide HGG). Preferred dipeptide include for example N-Palmitoyl-beta-Ala-His, N-Acetyl-Tyr-Arg-hexadecylester (Calmosensine™, Idealift™ from Sederma). Preferred tripeptide derivatives include for example N-Palmitoyl-Gly-Lys-His, and Pal-Gly-His-Lys, (Pal-GKH and Pal-GHK from Sederma), the copper derivative of HGG (Lamin™ from Sigma), Lipospondin (N-Elaidoyl-KTFK (SEQ ID NO: 10)) and its analogs of conservative substitution, N-Acetyl-RKR—NH$_2$ (Peptide CK+), N-Biot-GHK (from Sederma), Pal-KMO2K (Matrixyl Synthe6™ from Sederma) and derivatives thereof. Suitable tetrapeptide derivatives for use according to the present invention include, but are not limited to, N-Pal-GQPR (SEQ ID NO: 2) (from Sederma), suitable pentapeptide derivatives for use herein include, but are not limited to, Pal-KTTKS (SEQ ID NO: 1) (available as Matrixyl™ from Sederma), Pal-YGGFL (SEQ ID NO: 11) or Pal-YGGFP (SEQ ID NO: 12) or mixtures thereof. Suitable hexapeptide derivatives for use herein include, but are not limited to, Pal-VGVAPG (SEQ ID NO: 9), HLDIIW (SEQ ID NO: 13), HLDIITpi (SEQ ID NO: 14), Tpi being the Tryptoline-3-carboxylic acid residue, or HLDIIF (SEQ ID NO: 15), or Pal-, and derivatives thereof. The mixture of Pal-GHK and Pal-GQPR (SEQ ID NO: 2) (Matrixyl™ 3000, Sederma) can also be mentioned.

The preferred compositions commercially available containing a tripeptide or a derivative include Biopeptide-CL™, Maxilip™, Biobustyl™, Procapil™ and Matrixyl™ synthe'6™ of Sederma. The compositions commercially available preferred sources of tetrapeptides include Rigin™, Eyeliss™, Matrixyl™ Reloaded and Matrixyl 3000™ which contain between 50 and 500 ppm of Pal-GQPR (SEQ ID NO: 2) and an excipient, proposed by Sederma.

The following marketed peptides can be mentioned as well as additional active ingredients:

Vialox™ (INCI name=Pentapeptide-3 (synthetic peptide comprising alanine, arginine, isoleucine, glycine and proline)), Syn-akc™ (β-Ala-Pro-Dab-NH-Bzl) or Syn-Coll™ (Pal-Lys-Val-Lys-OH) marketed by Pentapharm;

Argireline™ (Ac-Glu-Glu-Met-Gln-Arg-Arg-NH$_2$ (INCI name=Acetyl hexapeptide-3) (SEQ ID NO: 16), Leuphasyl™ (Tyr-D-Ala-Gly-Phe-Leu) (SEQ ID NO: 17), Aldenine™ (Gly-His-Lys), Trylagen™ (INCI name=*Pseudoalteromonas* Ferment Extract, Hydrolyzed Wheat Protein, Hydrolyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO: 18), Serilesine™ (Ser-Ile-Lys-Val-Ala-Val) (SEQ ID NO: 19) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;

Collaxyl™ (Gly-Pro-Gln-Gly-Pro-Gln (SEQ ID NO: 20)) or Quintescine™ (Cys-Gly) marketed by Vincience;

Cytokinol™ LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'Institut Européen de Biologic Cellulaire;

Neutrazen™ (Pal-His-D-Phe-Arg-NH$_2$) marketed by Innovations; or

BONT-L-Peptidc™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by Infinitec Activos.

More specifically, the peptidic compound(s) according to the invention may be combined with at least one of compounds selected from compounds of the vitamin B3, compounds such as niacinamide or tocopherol, retinoid compounds such as retinol, hexamidine, α-lipoic acid, resveratrol or DHEA, hyaluronic acid, peptides, in particular N-acetyl-Tyr-Arg-O-hexadecyl ester, Pal-VGVAPG (SEQ ID NO: 9), Pal-KTIKS (SEQ ID NO: 1), Pal-GHK, Pal-KMO2K and Pal-GQPR (SEQ ID NO: 2), which are widely used active ingredients in topical cosmetic or dermopharmaceutical compositions.

The present invention also encompasses a method of topical cosmetic treatment, cosmeceutical (oral), or therapeutical, for improving the appearance and general condition of the skin and its appendages, comprising the topical application to the skin of a subject in need thereof of an effective amount of a peptidic compound or a mixture of peptidic compounds of the invention or a composition according to the invention comprising the said peptidic compound or mixture of peptidic compounds, the peptidic compounds being as defined above.

«Topical treatment» or "topical use" means according to the invention, an application that is intended to act where it is applied: skin, mucosa and/or appendages.

The peptide or composition of the invention may be applied locally to targeted areas.

The "effective" amount of the active peptidic compound or mixture of peptidic compounds in the composition, that is to say its dosage, depends on various factors, such as the age, the condition of the skin and appendages of the person, seriousness of the disorder(s) or phatology, the administration mode, etc. An effective amount means a non-toxic amount enough to achieve the desired effect.

In a cosmetic composition according to the invention, the peptidic compound(s) to be present in an effective amount, are generally present in an amount ranging from 0.000001% and 15% with regard to the total weight of the composition, preferably from 0.00001% to 5%, more preferably from 0.0001% to 0.01% (from 1 to 100 ppm) for a topical cosmetic application, depending on the destination of the composition and the desired effect more or less pronounced. The peptidic compounds may be present in the compositions according to the invention in varying relative proportions, in equivalent amounts, or on the contrary in different proportions.

All percentages and ratios used herein are by weight of the total composition and all measurements are made at 25° C. unless it is otherwise specified.

For example, for a cosmetic treatment of the face, the European Cosmetics Directive has set a standard amount for applying a cream of 2.72 mg/cm$^2$/day/person and for a body lotion of 0.5 mg/cm$^2$/day/person.

According to other specific features, the cosmetic treatment method according to the invention can be combined with one or more other treatment methods targeting the skin such as lumino-therapy, heat or aromatherapy treatments.

According to the invention, devices with several compartments or kits may be proposed to apply the method described above which may include for example and non-restrictively, a first compartment containing a composition comprising one peptidic compound of the invention or a mixture thereof, and in a second compartment a composition containing another active ingredient and/or excipient, the compositions contained in the said first and second compartments in this case being considered to be a combination composition for simultaneous, separate or stepwise use in time, particularly in one of the treatment methods recited above.

The cosmetic treatment method according to the invention is more particularly adapted to slow down the degradation of the molecules of the dermal extracellular matrix or to stimulate their synthesis and/or to act on the DEJ via the stimulation of collagen IV and/or laminin and more particularly adapted to:
Global anti-aging treatment; and/or
Anti-wrinkles and fine lines treatment (smoothed skin relief; filled wrinkles), and/or
A treatment improving the mechanical properties of skin: firmness/tone/elasticity/flexibility, and/or
A treatment increasing skin density (restructuring effect); and/or
A treatment increasing the volume of skin (plumping effect); and/or
A treatment to fight against the appearance of stretch marks, and/or
A moisturizing treatment, and/or
An anti-spot treatment, and/or
A treatment to improve the homogeneity and/or radiance of skin, and/or
A treatment acting on the pigmentation of the skin.

Other uses are of course possible for the peptidic compounds of the invention (alone or in combination), for example moisturizing, slimming, detoxifying, anti-glycation, anti-radical, toning, against tired skins, under-eye bags and/or dark circles, calming, hair growth, radiance of complexion, pigmentation, scalp treatments, etc., for either prevention or cure.

A composition according to the invention comprising at least one peptidic compound defined by formula I is suitable for a therapeutic treatment of a skin deficient in molecules constituting the dermal extracellular matrix.

EXAMPLES The following examples disclose and illustrate certain aspects of the invention. They should not be seen as limiting the disclosure, as they only provide useful information for its understanding and implementation.

A) General Protocol for the Synthesis of Peptidic Compounds According to the Invention Comprising a Modified Lysine The peptidic compounds are synthetised in solid phase using the Fmoc coupling chemistry (amine protective groupe (fluorenylmethoxycarbonyle) to protect the following aminaoacid in the direction on the N-terminal end of the peptide). The support comprising the first Fmoc-aminoacid (250 μM) is suspended in DMSO and is de-protected with a pyrrolidine solution (20% dans DMSO) during 30 mn, then rinsed several times with DMSO. The coupling of the following Fmoc-aminoacid (200 mM/DMSO) is realized with HATU (0.5M/DMSO) (agent used to transform the carboxylic acid into an active ester) in the presence of N-methylmorpholine (2M/DMSO) during 2 h. When the coupling is completed, the resin is rinsed several times using DMSO.

This operating cycle is realized to couple each aminoacid of the sequence of the peptidic compound and also to couple the N-terminal group (for example a palmitoyl (Pal)). A linear peptidic compound is thus obtained completely protected on a support.

To carry out the modification of the lysine, care will previously be taken to incorporate in the sequence a lysine derivative with a lateral amine protected with the methyltrityl group (Fmoc-Lys(Mtt)-OH). This Mtt group is released with a TFA-TIS-DCM solution (5-10-85) then the liberated amine is neutralized with the previous pyrrolidine solution. After rinsing with DMSO, the desired carboxylic acid is coupled, with the same procedure as above and the finishing rinsing with DCM are performed.

Final deprotection and cleavage from the support are carried out with a solution of TFA-TIS—H$_2$O (95-2.5-2.5) for 30 min. The solid support is filtered and the solution is evaporated under reduced pressure to remove TFA. The deprotected peptidic compound was then precipitated with ether. The suspension is centrifuged and rinsed with ether. The centrifugation process is repeated 3 times by changing ether and the crude peptidic compound is dried. It is then included in 0.1 N HCl, frozen and then lyophilized.

B) Preparation of a Composition According to the Invention Comprising a Peptidic Compound Prepared According to Example A).

Starting Products:
The pure peptidic compounds, synthetized according to the synthesis method explained above;
Excipient: a mixture of fatty esters, chosen in order to form an oily matrix, for example for forming a water free composition for the further formulation of water free cosmetic compositions.

Operating mode: The peptidic compound is mixed with the excipient and put under gentle stirring and heating until solubilization and total clarity.

C) In Vitro Evaluations

The peptidic compounds according to the invention show a number of remarkable effects presented below. Compounds prepared according to A) above and dissolved in an excipient were in vitro tested and showed activities that are presented below.

1) ELISA Assays

Protocol

Normal human fibroblasts (NHF) in culture are brought into contact with the products to be tested or their excipient (negative control) for 72 hours. After the contact, the culture supernatants are recovered and the synthesis of dermal macromolecules are estimated by ELISA. An estimation of cell viability is performed by Hoechst assay and is used to weight the obtained data.

Results

TABLE 1

Collagen I

| Product | Concentration | Change %/control | Significance (Student test) |
|---|---|---|---|
| Pal-K(P)-HG-OH | 3 ppm | +104 | $p < 0.05$ |
|  | 7 ppm | +71 | $p < 0.01$ |
|  | 10 ppm | +107 | $p < 0.01$ |
| Pal-K(Pyr)-HG-OH | 7 ppm | +71 | $p < 0.01$ |
|  | 10 ppm | +93 | $p < 0.01$ |

TABLE 2

Collagen IV

| Product | Concentration | Change %/control | Significance (Student test) |
|---|---|---|---|
| Pal-K(P)-HG-OH | 3 ppm | +36 | $p < 0.01$ |
|  | 7 ppm | +79 | $p < 0.01$ |
|  | 10 ppm | +182 | $p < 0.01$ |
| Pal-K(Pyr)-HG-OH | 12.5 ppm | +234 | $p < 0.01$ |

TABLE 3

Fibronectine

| Product | Concentration | Change %/control | Significance (Student test) |
|---|---|---|---|
| Pal-K(P)-HG-OH | 3 ppm | +32 | $p < 0.01$ |
|  | 7 ppm | +53 | $p < 0.01$ |
|  | 10 ppm | +59 | $p < 0.01$ |
| Pal-K(Pyr)-HG-OH | 7 ppm | +50 | $p < 0.01$ |
|  | 10 ppm | +71 | $p < 0.01$ |
|  | 12.5 ppm | +249 | $p < 0.01$ |
| Pal-K(P)-GH-OH | 7 ppm | +46 | $p < 0.01$ |
| Pal-K(Pyr)-GH-OH | 3 ppm | +22 | $p < 0.01$ |
|  | 7 ppm | +37 | $p < 0.01$ |
|  | 10 ppm | +54 | $p < 0.01$ |

TABLE 4

Laminines

| Product | Concentration | Change %/control | Significance (Student test) |
|---|---|---|---|
| Pal-K(Pyr)-HG-OH | 7 ppm | +23 | $p < 0.05$ |
|  | 10 ppm | +30 | $p < 0.05$ |
| Pal-K(Pyr)-GH-OH | 10 ppm | +33 | $p < 0.01$ |

TABLE 5

Elastin

| Product | Concentration | Change %/control | Significance (Student test) |
|---|---|---|---|
| Pal-K(P)-HG-OH | 10 ppm | +224 | $p < 0.05$ |
| Pal-K(Pyr)-HG-OH | 7 ppm | +156 | $p < 0.01$ |

TABLE 6

Hyaluronic acid

| Product | Concentration | Change %/control | Significance (Student test) |
|---|---|---|---|
| Pal-K(P)-HG-OH | 3 ppm | +53 | $p < 0.01$ |
|  | 5 ppm | +44 | $p < 0.01$ |
| Pal-K(Pyr)-HG-OH | 12.5 ppm | +310 | $p < 0.01$ |
| Pal-K(Pyr)-GH-OH | 7 ppm | +67 | $p < 0.01$ |
|  | 10 ppm | +168 | $p < 0.01$ |

Comparative ELISA Assays

Pal-K(P)-HG-OH and/or Pal-K(Pyr)-HG-OH are compared to the Pal-KHG-OH on the same ELISA assays.

TABLE 7

Collagen I

| Product | Concentration | Change %/control | Significance (Student test) |
|---|---|---|---|
| Pal-KHG-OH | 3 ppm | +27 | $p < 0.05$ |
|  | 10 ppm | +78 | $p < 0.01$ |
| Pal-K(P)-HG-OH | 3 ppm | +104 | $p < 0.05$ |
|  | 10 ppm | +107 | $p < 0.01$ |
| Pal-K(Pyr)-HG-OH | 10 ppm | +93 | $p < 0.01$ |

TABLE 8

Collagen IV

| Product | Concentration | Change %/control | Significance (Student test) |
|---|---|---|---|
| Pal-KHG-OH | 10 ppm | +116 | $p < 0.01$ |
| Pal-K(P)-HG-OH | 10 ppm | +182 | $p < 0.01$ |
| Pal-K(Pyr)-HG-OH | 12.5 ppm | +234 | $p < 0.01$ |

TABLE 9

Fibronectine

| Product | Concentration | Change %/control | Significance (Student test) |
|---|---|---|---|
| Pal-KHG-OH | 12.5 ppm | +64 | $p < 0.05$ |
| Pal-K(Pyr)-HG-OH | 12.5 ppm | +249 | $p < 0.01$ |

TABLE 10

Laminine

| Product | Concentration | Change %/control | Significance (Student test) |
|---|---|---|---|
| Pal-KHG-OH | 10 ppm | −38 | $p < 0.01$ |
| Pal-K(P)-HG-OH | 10 ppm | +32 | $p < 0.05$ |
| Pal-K(Pyr)-HG-OH | 10 ppm | +30 | $p < 0.05$ |

TABLE 11

Elastin

| Product | Concentration | Change %/control | Significance (Student test) |
|---|---|---|---|
| Pal-KHG-OH | 7 ppm | +113 | $p < 0.01$ |
|  | 12.5 ppm | +93 | $p < 0.01$ |

TABLE 11-continued

Elastin

| Product | Concentration | Change %/control | Significance (Student test) |
|---|---|---|---|
| Pal-K(P)-HG-OH | 10 ppm | +224 | $p < 0.05$ |
| Pal-K(Pyr)-HG-OH | 7 ppm | +156 | $p < 0.01$ |

TABLE 12

Hyaluronic acid

| Product | Concentration | Change %/control | Significance (Student test) |
|---|---|---|---|
| Pal-KHG-OH | 12.5 ppm | +225 | $p < 0.05$ |
| Pal-K(Pyr)-HG-OH | 12.5 ppm | +310 | $p < 0.01$ |

D) Galenic

Different formulations are described below. Additional cosmetic active ingredients, brought optionally in support and/or in addition to the activity of the active ingredient according to the invention can be added in the correct phase according to their hydrophobic or hydrophilic nature. These ingredients can be of any category according to their(s) function(s), site of application (body, face, neck, chest, hands, hair, eyelashes, eyebrows, hair, etc.), the desired final effect and the targeted consumer, for example antioxidant, moisturizing, nourishing, protective, smoothing, remodeling, volumizing (lipofiling), acting on skin radiance, anti-spots, anti-dark circles, anti-glycation, slimming, relaxing, myorelaxant, anti-redness, anti-stretch marks, etc. They are mentioned above in the description.

1) Cream Form, for Example an Antiaging Day Cream for the Face

| Ingredient (INCI name) | Weight % |
|---|---|
| Phase A | |
| Sorbitan Stearate | 3.00 |
| Cyclopentasiloxane (and) Cyclohexasiloxane | 2.00 |
| Ethylhexyl Palmitate | 3.00 |
| Glyceryl Stearate (and) PEG-100 Stearate | 3.00 |
| Ethylhexyl Methoxycinnamate | 1.00 |
| Ethylhexyl Dimethyl PABA | 1.00 |
| Phase B | |
| Demineralised water | Qsp 100 |
| Ultrez 10 (Carbomer) | 0.40 |
| Phase C | |
| Glycerin | 5.00 |
| Preservative | qs |
| Phase D | |
| Peptidic compound according to the invention in a fatty excipient | 3.00 |
| Phase E | |
| Potassium Sorbate | 0.10 |
| Phase F | |
| Sodium Hydroxide 30% | 0.60 |
| Demineralised water | 6.00 |
| Phase G | |
| Fragrance | 0.10 |

Protocol: Weigh phase A and heat at 75° C. in a water bath. Weigh phase B and let swell for 20 minutes. Melt phase C until dissolved and add to phase B. Heat phase (B+C) at 75° C. using a water bath. Pour phase A into phase (B+C) under Staro stirring. Extemporaneously, add phase D to phase (A+B+C). At approximately 45° C. add phase E and neutralize with phase F. Mix well. At 35° C., add phase G. Homogenize. pH: 6.20.

Examples of ingredients which may be added to this formulation:

CALMOSENSINE™: soothing active for sensitive skins marketed by Sederma (WO1998/07744) comprising the Tyr-Arg lipo-dipeptide. It reduces discomfort feelings.

SEBULESS™: purifying sebo-regulator ingredient comprising a *Syringa vulgaris* extract, marketed by Sederma, which mattifies and refreshes complexion, fades the blemishes.

PRODIZIA™: active ingredient marketed by SEDERMA (WO2013/046137), comprising an extract of *Albizia julibrissin*, fighting the signs cutaneous fatigue: dark circles, under eye bags, dull complexion and drawn features, by repairing and protection the skin against the caused by damages of glycation and glycoxydation.

PACIFEEL™: active ingredient actif marketed by Sederma, comprising a natural extract of the *Mirabilis jalapa* plant also known as the Marvel of Peru, which alleviates cutaneous discomfort, fades redness of sensitive and reactive skin and strengthens and hydrates the epidermis.

2) Gel from, for Example a Firming Gel for the Body

| Ingredient (INCI name) | Weight % |
|---|---|
| Phase A | |
| Demineralised water | Qsp 100 |
| Ultrez 10 (Carbomer) | 0.20 |
| Phase B | |
| PEG 400 | 5.00 |
| Preservatives | qs |
| Phase C | |
| Dimethicone | 4.00 |
| Pemulen TR2 (Acrylates/C10-30 Alkyl Acrylate Cross Polymer) | 0.20 |
| Phase D | |
| Tween 20 (Polysorbate 20) | 1.00 |
| Peptidic compound in a fatty excipient | 2.00 |
| Phase E | |
| Potassium Sorbate | 0.10 |
| Phase F | |
| Sodium Hydroxide 30% | 0.60 |
| Demineralised water | 5.00 |
| Phase G | |
| Fragrance | 0.10 |

Protocol: Disperse Ultrez 10 in water and let swell for 15 minutes. Heat phase B until dissolved and add to phase A. Weigh and mix phase C. Stir Phase D and add to phase C; mix well. Add phase (C+D) to phase (A+B). Then add phase E. Let swell for 1 hour. Mix well. Neutralize with phase F. Finally, add phase G. pH 6.10.

Examples of ingredients which may be added to this formulation:

AQUALANCE™: osmo-protector moisturising active ingredient marketed by Sederma (WO2009/104118) comprising homarine and erythritol.

LEGANCE™: anti-aging active marketed by Sederma (WO2013/105047), corresponding to a *Zingiber zerumbet* Smith extract obtained by $CO_2$ supercritical in a water-soluble excipient and titrated in zerumbone ingredient. It is a global anti-aging ingredient for legs. It improves their appearance and comfort by reducing water retention, improving microcirculation and refining adipose tissue.

BODYFIT™: slimming/firming active ingredient comprising glaucine marketed by Sederma (WO 2004/024695). BODYFIT™ reduces the appearance of cellulite and helps to improve drainage and water distribution in the tissues.

JUVINITY™: active marketed by SEDERMA reducing signs of aging on the face and neckline, smoothing wrinkles, densifying and restructuring the dermis.

1) Compact Powder Form

| Ingredient (INCI name) | Weight % |
| --- | --- |
| Phase A | |
| Talc | Qsp 100 |
| Kaolin | 2.00 |
| Calcium Stearate | 1.00 |
| Mica | 4.00 |
| Silica | 1.00 |
| Bismuth Oxychloride | 2.00 |
| Potassium Sorbate | qs |
| Phenoxyethanol | qs |
| Phase B | |
| Unipure Black LC 989 HLC [CI 77499 (and) Hydrogenated Lecithin] | 0.20 |
| Unipure Red LC 381 HLC [CI 77491 (and) Hydrogenated Lecithin] | 0.60 |
| Unipure Yellow LC 182 HLC [CI 77492 (and) Hydrogenated Lecithin] | 1.00 |
| Covapearl Star Gold 2302 AS [CI 77891 (and) CI 77491 (and) Synthetic Fluorphlogopite (and) Triethoxycaprylylsilane] | 0.50 |
| Covapearl Brown 838 HLC [CI 77491 (and) Mica (and) Hydrogenated Lecithin] | 1.00 |
| Covapearl Dark Blue 637 [CI 77510 (&) CI 77891 (&) Mica] | 0.10 |
| Phase C | |
| Crodamol PTIS-LQ-(MV) [Pentaerythrityl Tetraisostearate] | 4.00 |
| Peptidic compound according to the invention in a fatty matrix | 3.00 |
| Phase D | |
| Fragrance | 0.30 |

Protocol: Weigh phase A and mix. Weigh phase B and pour into phase B. Pour A+B into the blender and mix. Add phase C to A+B in several times and mix each time. Add phase D. Check homogeneity at every step.

Example of ingredients which may be added to this formulation:

VEGESOME MOIST 24™: ingredient marketed by SEDERMA designed for the formulation of moisturizing powder makeup; it is a powder consisting of hollow particles 25 microns (*Lycopodium clavatum* exins) loaded with an *Imperata cylindrica* extract having moisturizing properties.

3) Alternative Cream Form (Face or Body)

| Ingredient (INCI name) | Weight % |
| --- | --- |
| Phase A | |
| Arlacel 170 (Glyceryl Stearate (and) PEG-100 Stearate) | 5.50 |
| Abil Wax 2434 (Stearoxy Dimethicone) | 3.00 |
| Acetulan (Cetyl Acetate (and) Acetylated Lanolin Alcohol) | 1.50 |
| Crodacol C 90 (Cetyl Alcohol) | 1.50 |
| Mineral Oil | 3.00 |
| Shea Butter | 5.00 |
| Unsaponifiable Shea | 1.00 |
| Parsol MCX (Ethylhexyl Methoxicinnamate) | 3.50 |
| Phase B | |
| Demineralised water | Qs 100 |
| Phase C | |
| Carbopol 940 (Carbomer) | 0.20 |
| Phase D | |
| Deminarilised water | 2.00 |
| Triethanolamine 99% | 0.20 |
| Phase E | |
| Propylene Glycol | 0.10 |
| Mixed Parabens | |
| Phase F | |
| Sodium hydroxyde 30% | 5.00 |
| Demineralised water | qs |
| Phase G | |
| Peptidic compound according to the invention in an hydrophilic matrix | 2.00 |

Protocol: Weigh phase A and heat at 75° C. using a water bath. Weigh phase B and let swell for 20 minutes. Melt phase C until dissolved and add to phase B. Heat phase (B+C) at 75° C. using a water bath. Pour phase A into phase (B+C) under Staro stirring. Extemporaneously, add phase D to phase (A+B+C). Approximately at 45° C. add phase E and neutralize with phase F. Mix well. At 35° C., add phase G. Homogenize well. pH: 6.20.

Examples of ingredients which may be added to this formulation:

SUBLISKIN™: active ingredient marketed by SEDERMA (WO2010/067327) that moisturizes and smooths the skin while allowing it to resist to external aggressions.

VENUCEANE™: active marketed by Sederma (WO2002/066668) comprising a *Thermus thermophiles* biotechnological extract, that prevents visible signs of photo-aging (spots, wrinkles, dryness . . . ), protects cell structures from damages caused by UV and strengthens skin integrity.

KOMBUCHKA™: active ingredient acting on complexion marketed by SEDERMA (WO2004/012650).

INTENSLIM™: slimming active ingredient marketed by Sederma (WO2013/105048) corresponding to a synergistic combination of extracts obtained by *Globularia cordifolia* plant cell culture, *Zingiber zerumbet* Smith titrated in zerumbone and vegetable caffeine obtained by supercritical $CO_2$ extraction.

The invention claimed is:

1. A peptidic compound represented by formula (I):

$$X-(AA)_n-(AA)^*-(AA)_m-Z \quad (I)$$

wherein:
- (AA)* is lysine (K*), on which a carboxylic acid is grafted by a peptidic bond on the nitrogen of the lateral chain, wherein the carboxylic acid is selected from the group consisting of proline (P, Pro), hydroxyproline (Hyp), pyroglutamic acid (Pyr), histidine (H, His), phenylalanine (F, Phe), tyrosine (Y, Tyr), tryptophan (W, Trp), tetrahydroisoquinoline-3 carboxylic acid (Tic), tetrahydronorharman-3 carboxylic acid (Tpi), pipecolic acid (Hpr), nipecotic acid (Nip), picolinic acid (Pic), 4-imidazole carboxylic acid (Im4COOH), stachydrine (Sta), betonicine (Btn) and homarine (Hom);
- $n = 0, 1, 2, 3$ or $4$;
- $m = 0, 1, 2, 3$ or $4$;
- AA is (AA)* or an amino acid selected from the group consisting of glycine (G, Gly), histidine (H, His), lysine (K, Lys), hydroxylysine (Hyl), serine (S, Ser), hydroxyproline (Hyp) and tyrosine (Y, Tyr), each AA being selected independently from each other; and
- $n+m > 1$;

at the N terminal end, X is selected from the group consisting of H, —CO—$R_1$ and —$SO_2$—$R_1$;

at the C terminal end, Z is selected from the group consisting of OH, $OR_1$, $NH_2$, $NHR_1$ and $NR_1R_2$; and $R_1$ and $R_2$ are, independently from each other, selected from the group consisting of an alkyl, aryl, aralkyl, alkylaryl, alkoxy and aryloxy radical, that can be linear, branched, cyclic, polycyclic, unsaturated, hydroxylated, carbonylated, phosphorylated and/or sulphated, wherein said radical optionally comprises a heteroatom in the backbone thereof, with the proviso that H—FK(F)—OH is excluded.

2. The peptidic compound of claim 1, wherein AA=(AA)* or an amino acid selected from the group consisting of glycine (G, Gly), histidine (H, His) and serine (S, Ser).

3. The peptidic compound of claim 1, wherein K* is selected from the group consisting of:

K(P): a proline (P, Pro) grafted on a lysine (K, Lys),

K(Hyp): a hydroxyproline (Hyp) grafted on a lysine (K, Lys), and

K(Pyr): a pyroglutamic acid (Pyr) grafted on a lysine (K, Lys).

4. The peptidic compound of claim 1, wherein $R_1$ and/or $R_2$ is an alkyl chain having 1 to 24 carbon atoms.

5. The peptidic compound oft, wherein $R_1$ and/or $R_2$ is an alkyl chain having 3 to 24 carbon atoms.

6. The peptidic compound of claim 1, wherein X is an acyl CO—$R_1$ radical and Z is selected from the group consisting of OH, OMe, OEt and $NH_2$.

7. The peptidic compound of claim 6, wherein Z is OH.

8. The peptidic compound of claim 3, wherein X is an acyl CO—$R_1$ radical selected from the group consisting of an octanoyl (C8), decanoyl (C10), lauroyl (C12), myristoyl (C14), palmitoyl (C16), stearoyl (C18), biotinoyl, elaidoyl, oleoyl and lipoyl.

9. The peptidic compound of claim 8, wherein X is selected from the group consisting of a myristoyl (C14) and a palmitoyl (C16) group.

10. The peptidic compound of claim 1, wherein n=0.

11. The peptidic compound of claim 10, selected from the group consisting of X—K(P)-HG-Z, X—K(Pyr)-HG-Z, X—K(Hyp)-HG-Z, X—K(P)-GH—Z, X—K(Pyr)-GH—Z and X—K(Hyp)-GH—Z.

12. The peptidic compound of claim 11, wherein the compound is selected from the group consisting of Pal-K(P)-HG-OH, Pal-K(Pyr)-HG-OH, Pal-K(Hyp)-HG-OH, Pal-K(P)-GH-OH, and Pal-K(Pyr)-GH-OH and Pal-K(Hyp)-GH-OH.

13. The peptidic compound of claim 1, which is Pal-K(P)-HG-OH.

14. A cosmetic or dermopharmaceutical composition comprising at least one peptidic compound of claim 1 in a physiologically acceptable medium.

* * * * *

UNITED STATES PATENT AND TRADEMARK OFFICE
CERTIFICATE OF CORRECTION

| | |
|---|---|
| PATENT NO. | : 11,612,556 B2 |
| APPLICATION NO. | : 15/535651 |
| DATED | : March 28, 2023 |
| INVENTOR(S) | : Olivier Peschard et al. |

It is certified that error appears in the above-identified patent and that said Letters Patent is hereby corrected as shown below:

In the Claims

Claim 5 Column 33, Line 26: "oft," should be replaced with --of claim 4,--

Signed and Sealed this
Thirtieth Day of May, 2023

Katherine Kelly Vidal
*Director of the United States Patent and Trademark Office*